(12) United States Patent
Conston et al.

(10) Patent No.: US 7,892,247 B2
(45) Date of Patent: Feb. 22, 2011

(54) DEVICES AND METHODS FOR INTERCONNECTING VESSELS

(75) Inventors: Stanley R. Conston, San Carlos, CA (US); Ronald K. Yamamoto, San Francisco, CA (US); Jodi J. Akin, Alamo, CA (US); Gitanjali V. Barry, Fremont, CA (US)

(73) Assignee: BioConnect Systems, Inc., Ambler, PA (US)

( * ) Notice: Subject to any disclaimer, the term of this patent is extended or adjusted under 35 U.S.C. 154(b) by 894 days.

(21) Appl. No.: 10/264,741

(22) Filed: Oct. 3, 2002

(65) Prior Publication Data

US 2003/0088256 A1    May 8, 2003

Related U.S. Application Data

(60) Provisional application No. 60/327,126, filed on Oct. 3, 2001.

(51) Int. Cl.
*A61B 17/08* (2006.01)
(52) U.S. Cl. ...................... 606/155; 606/153
(58) Field of Classification Search ......... 606/152–156, 606/213; 623/1.35, 23.64, 1.15, 1.22, 1.2, 623/1.13, 1.16
See application file for complete search history.

(56) References Cited

U.S. PATENT DOCUMENTS

| | | | |
|---|---|---|---|
| 2,127,903 A | 8/1938 | Bowen | |
| 3,974,835 A | 8/1976 | Hardy, Jr. | |
| 4,352,358 A | 10/1982 | Angelchik | |
| 4,366,819 A | 1/1983 | Kaster | |
| 4,368,736 A | 1/1983 | Kaster | |
| 4,667,673 A | 5/1987 | Li | |
| 4,705,040 A | 11/1987 | Mueller et al. | |
| 4,787,386 A | 11/1988 | Walsh et al. | |
| 4,852,568 A | 8/1989 | Kensey | |
| 4,890,612 A | 1/1990 | Kensey | |
| 5,061,274 A | 10/1991 | Kensey | |
| 5,108,421 A | 4/1992 | Fowler | |
| 5,141,516 A | 8/1992 | Detweiler | |

(Continued)

FOREIGN PATENT DOCUMENTS

EP    0894475    2/1999

(Continued)

OTHER PUBLICATIONS

International Preliminary Examination Report for PCT/US02/03919 dated Feb. 9, 2003.

(Continued)

*Primary Examiner*—Anhtuan T Nguyen
*Assistant Examiner*—Tuan V Nguyen
(74) *Attorney, Agent, or Firm*—Kilpatrick Townsend & Stockton LLP

(57) ABSTRACT

The present invention provides implantable devices and associated methods for interconnecting human vessels in a side-to-side or an end-to-side arrangement rapidly, safely and in a minimally invasive manner. The devices comprise a vessel connector and a intravascular support mechanism for establishing fluid communication between two vessels. Certain embodiments further include a sealing member for further sealing the openings in the vessels created for inserting the subject devices.

32 Claims, 4 Drawing Sheets

U.S. PATENT DOCUMENTS

| | | |
|---|---|---|
| 5,192,302 A | 3/1993 | Kensey et al. |
| 5,197,976 A | 3/1993 | Herweck et al. |
| 5,222,974 A | 6/1993 | Kensey et al. |
| 5,282,827 A | 2/1994 | Kensey et al. |
| 5,330,445 A | 7/1994 | Haaga |
| 5,453,090 A | 9/1995 | Martinez et al. |
| 5,456,714 A | 10/1995 | Owen |
| 5,503,635 A | 4/1996 | Sauer et al. |
| 5,549,633 A | 8/1996 | Evans et al. |
| 5,586,987 A | 12/1996 | Fahy |
| 5,620,461 A | 4/1997 | Muijs Van De Moer et al. |
| 5,634,936 A | 6/1997 | Linden et al. |
| 5,649,959 A | 7/1997 | Hannam et al. |
| 5,669,924 A | 9/1997 | Shaknovich |
| 5,676,670 A | 10/1997 | Kim |
| 5,683,451 A | 11/1997 | Lenker et al. |
| 5,716,325 A | 2/1998 | Bonutti |
| 5,728,134 A | 3/1998 | Barak |
| 5,796,178 A | 8/1998 | Onuma |
| 5,797,934 A | 8/1998 | Rygaard |
| 5,830,222 A | 11/1998 | Makower |
| 5,853,422 A | 12/1998 | Huebsch et al. |
| 5,868,761 A | 2/1999 | Nicholas et al. |
| 5,868,763 A | 2/1999 | Spence et al. |
| 5,868,777 A | 2/1999 | Lam |
| 5,893,886 A | 4/1999 | Zegdi et al. |
| 5,921,995 A | 7/1999 | Kleshinski |
| 6,007,544 A | 12/1999 | Kim |
| 6,007,576 A | 12/1999 | McClellan |
| 6,017,352 A | 1/2000 | Nash et al. |
| 6,030,395 A | 2/2000 | Nash et al. |
| 6,036,702 A | 3/2000 | Bachinski et al. |
| 6,036,705 A | 3/2000 | Nash et al. |
| 6,056,762 A | 5/2000 | Nash et al. |
| 6,063,114 A | 5/2000 | Nash et al. |
| 6,068,638 A | 5/2000 | Makower |
| 6,068,654 A | 5/2000 | Berg et al. |
| 6,077,291 A | 6/2000 | Das |
| 6,113,612 A | 9/2000 | Swanson et al. |
| 6,117,145 A | 9/2000 | Wood et al. |
| 6,152,945 A | 11/2000 | Bachinski et al. |
| 6,165,185 A * | 12/2000 | Shennib et al. ............ 606/155 |
| 6,171,329 B1 | 1/2001 | Shaw et al. |
| 6,176,864 B1 | 1/2001 | Chapman |
| 6,190,353 B1 | 2/2001 | Makower et al. |
| 6,190,397 B1 | 2/2001 | Spence et al. |
| 6,193,734 B1 | 2/2001 | Bolduc et al. |
| 6,206,893 B1 | 3/2001 | Klein et al. |
| 6,206,913 B1 | 3/2001 | Yencho et al. |
| 6,214,022 B1 | 4/2001 | Taylor et al. |
| 6,214,029 B1 | 4/2001 | Thill et al. |
| 6,217,585 B1 | 4/2001 | Houser et al. |
| 6,231,587 B1 | 5/2001 | Makower |
| 6,241,741 B1 | 6/2001 | Duhaylongsod et al. |
| 6,241,768 B1 | 6/2001 | Agarwal et al. |
| 6,254,630 B1 * | 7/2001 | Inoue ....................... 623/1.15 |
| 6,270,515 B1 | 8/2001 | Linden et al. |
| 6,283,983 B1 | 9/2001 | Makower et al. |
| 6,302,905 B1 | 10/2001 | Goldsteen et al. |
| 6,350,280 B1 | 2/2002 | Nash et al. |
| 6,371,965 B2 | 4/2002 | Gifford, III et al. |
| 6,395,019 B2 | 5/2002 | Chobotov |
| 6,402,767 B1 | 6/2002 | Nash et al. |
| 6,409,739 B1 | 6/2002 | Nobles et al. |
| 6,419,681 B1 | 7/2002 | Vargas et al. |
| 6,428,550 B1 | 8/2002 | Vargas et al. |
| 6,440,163 B1 | 8/2002 | Swanson et al. |
| 6,443,965 B1 | 9/2002 | Gifford, III et al. |
| 6,458,140 B2 | 10/2002 | Akin et al. |
| 6,461,320 B1 | 10/2002 | Yencho et al. |
| 6,485,496 B1 | 11/2002 | Suyker et al. |
| 6,497,710 B2 | 12/2002 | Yencho et al. |
| 6,508,824 B1 | 1/2003 | Flaherty et al. |
| 6,517,558 B2 * | 2/2003 | Gittings et al. ............ 606/153 |
| 6,537,287 B1 | 3/2003 | Yencho et al. |
| 6,537,288 B2 | 3/2003 | Vargas et al. |
| 6,565,581 B1 | 5/2003 | Spence et al. |
| 6,585,762 B1 | 7/2003 | Stanish |
| 6,589,277 B1 | 7/2003 | Fabian et al. |
| 6,616,675 B1 * | 9/2003 | Evard et al. ................ 606/155 |
| 6,620,129 B2 | 9/2003 | Stecker et al. |
| 6,626,920 B2 | 9/2003 | Whayne |
| 6,626,939 B1 | 9/2003 | Burnside et al. |
| 6,652,543 B2 | 11/2003 | Spence et al. |
| 6,655,386 B1 | 12/2003 | Makower et al. |
| 6,695,875 B2 * | 2/2004 | Stelter et al. ................ 623/1.13 |
| 6,699,257 B2 | 3/2004 | Gifford, III et al. |
| 6,709,441 B2 | 3/2004 | Bolduc et al. |
| 6,712,831 B1 * | 3/2004 | Kaplan et al. ................ 606/153 |
| 6,719,781 B1 | 4/2004 | Kim |
| 6,726,697 B2 | 4/2004 | Nicholas et al. |
| 6,736,825 B2 | 5/2004 | Blatter et al. |
| 6,740,101 B2 | 5/2004 | Houser et al. |
| 6,776,785 B1 | 8/2004 | Yencho et al. |
| 6,786,914 B1 | 9/2004 | Vargas et al. |
| 6,790,229 B1 | 9/2004 | Berreklouw |
| 6,913,607 B2 | 7/2005 | Ainsworth et al. |
| 6,916,327 B2 | 7/2005 | Northrup, III et al. |
| 6,926,724 B1 | 8/2005 | Chu |
| 6,962,596 B2 | 11/2005 | Bolduc et al. |
| 6,972,023 B2 | 12/2005 | Whayne et al. |
| 7,008,436 B2 | 3/2006 | Barath |
| 7,018,388 B2 | 3/2006 | Yencho et al. |
| 7,025,773 B2 | 4/2006 | Gittings et al. |
| 7,029,482 B1 | 4/2006 | Vargas et al. |
| 7,041,110 B2 | 5/2006 | Yencho et al. |
| 7,063,712 B2 | 6/2006 | Vargas et al. |
| 7,128,749 B1 | 10/2006 | Vargas et al. |
| 7,160,311 B2 | 1/2007 | Blatter et al. |
| 7,172,608 B2 | 2/2007 | Vargas et al. |
| 7,175,637 B2 | 2/2007 | Vargas et al. |
| 2001/0004699 A1 | 6/2001 | Gittings et al. |
| 2001/0047165 A1 | 11/2001 | Makower et al. |
| 2001/0049539 A1 | 12/2001 | Rehil |
| 2002/0022853 A1 | 2/2002 | Swanson et al. |
| 2002/0029079 A1 | 3/2002 | Kim et al. |
| 2002/0091398 A1 | 7/2002 | Galdonik et al. |
| 2003/0065344 A1 | 4/2003 | Kirsch et al. |
| 2003/0212418 A1 | 11/2003 | Yencho et al. |
| 2003/0229365 A1 | 12/2003 | Whayne et al. |
| 2003/0236542 A1 | 12/2003 | Makower |
| 2004/0024345 A1 | 2/2004 | Gharib et al. |
| 2004/0073238 A1 | 4/2004 | Makower |
| 2004/0073282 A1 | 4/2004 | Stanish |
| 2004/0088042 A1 | 5/2004 | Kim et al. |
| 2004/0097991 A1 | 5/2004 | Vargas et al. |
| 2004/0102796 A1 | 5/2004 | Hill et al. |
| 2004/0122318 A1 | 6/2004 | Flaherty et al. |
| 2004/0133225 A1 | 7/2004 | Makower |
| 2004/0158143 A1 | 8/2004 | Flaherty et al. |
| 2004/0249400 A1 | 12/2004 | Vargas et al. |
| 2004/0260318 A1 | 12/2004 | Hunter et al. |
| 2005/0043751 A1 | 2/2005 | Phan et al. |
| 2005/0043752 A1 | 2/2005 | Phan et al. |
| 2005/0137614 A1 | 6/2005 | Porter et al. |
| 2005/0149073 A1 | 7/2005 | Arani et al. |
| 2005/0165426 A1 | 7/2005 | Manzo |
| 2005/0251187 A1 | 11/2005 | Beane et al. |
| 2006/0064119 A9 | 3/2006 | Tilson et al. |
| 2006/0241342 A1 | 10/2006 | Macaulay et al. |

FOREIGN PATENT DOCUMENTS

| | | |
|---|---|---|
| JP | 03-018355 | 1/1991 |

| | | |
|---|---|---|
| JP | 9-511409 | 11/1997 |
| JP | 02003220065 | 8/2003 |
| WO | 9014796 | 12/1990 |
| WO | 9514442 | 6/1995 |
| WO | 9727898 | 8/1997 |
| WO | 9802099 | 1/1998 |
| WO | 9807399 | 2/1998 |
| WO | 9816174 | 4/1998 |
| WO | 9819629 | 5/1998 |
| WO | 9819636 | 5/1998 |
| WO | 9840036 | 9/1998 |
| WO | 9852471 | 11/1998 |
| WO | 9852474 | 11/1998 |
| WO | 9908603 | 2/1999 |
| WO | 9911180 | 3/1999 |
| WO | 9948427 | 9/1999 |
| WO | 0027310 | 5/2000 |
| WO | 0027313 | 5/2000 |
| WO | WO 00/41633 | 7/2000 |
| WO | 0053104 | 9/2000 |
| WO | 0069365 | 11/2000 |
| WO | 0139672 | 6/2001 |
| WO | WO 01/41653 | 6/2001 |

OTHER PUBLICATIONS

International Search Report for PCT/US00/20588 dated Aug. 30, 2000.
International Search Report for PCT/US02/03919 dated Dec. 12, 2002.
International Search Report for PCT/US08/072166 dated Oct. 24, 2008.
International Search Report for PCT/US08/072167 dated Oct. 24, 2008.
JP Office Action dated Dec. 19, 2008.
International Preliminary Report on Patentability for PCT/US2008/072166 dated Feb. 2, 2010.
Written Opinion for PCT/US2008/072166 dated Feb. 2, 2010.
International Preliminary Report on Patentability for PCT/US2008/072167 dated Feb. 2, 2010.
Written Opinion for PCT/US2008/072167 dated Feb. 2, 2010.

* cited by examiner

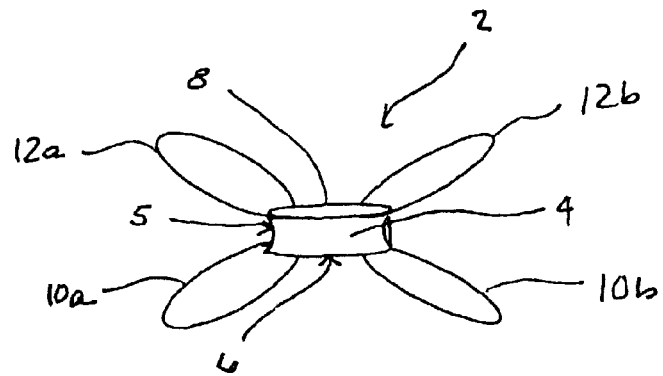
FIG._1A
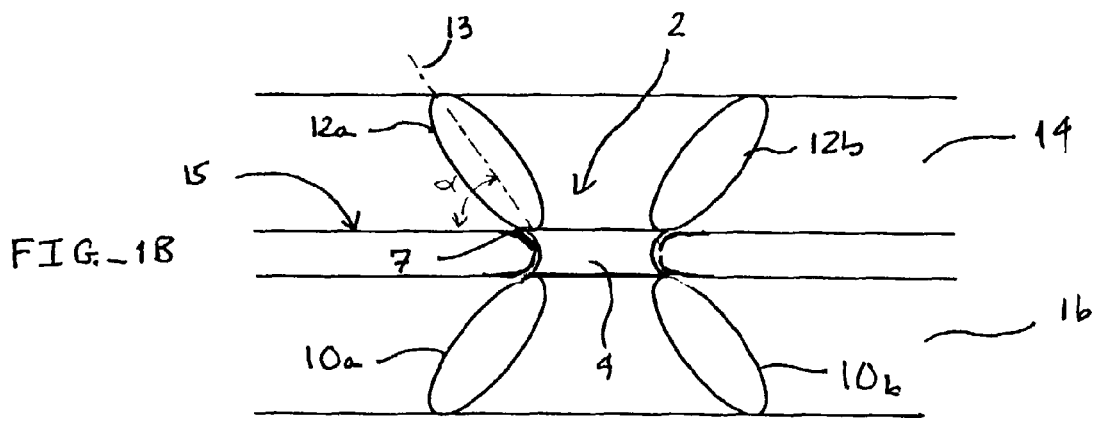
FIG._1B
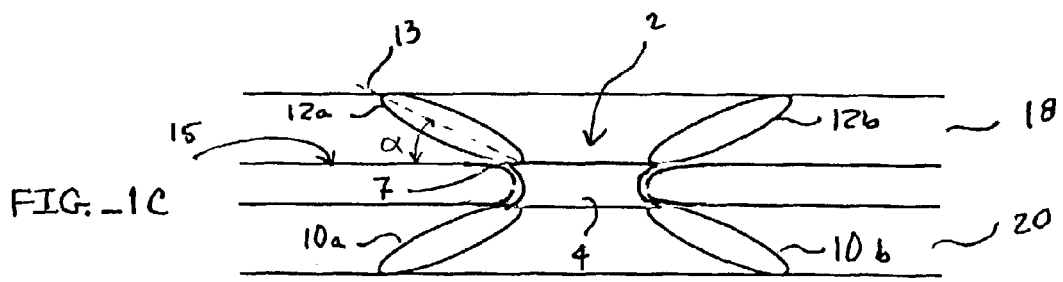
FIG._1C
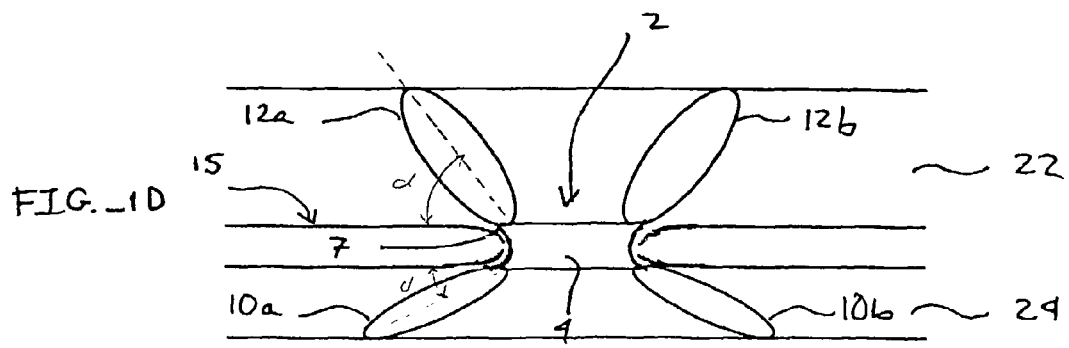
FIG._1D

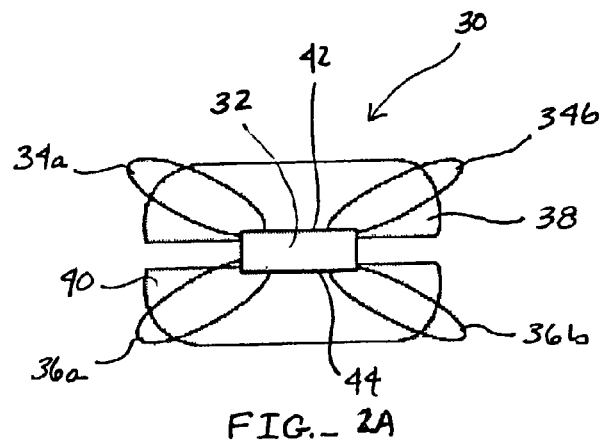
FIG.—2A
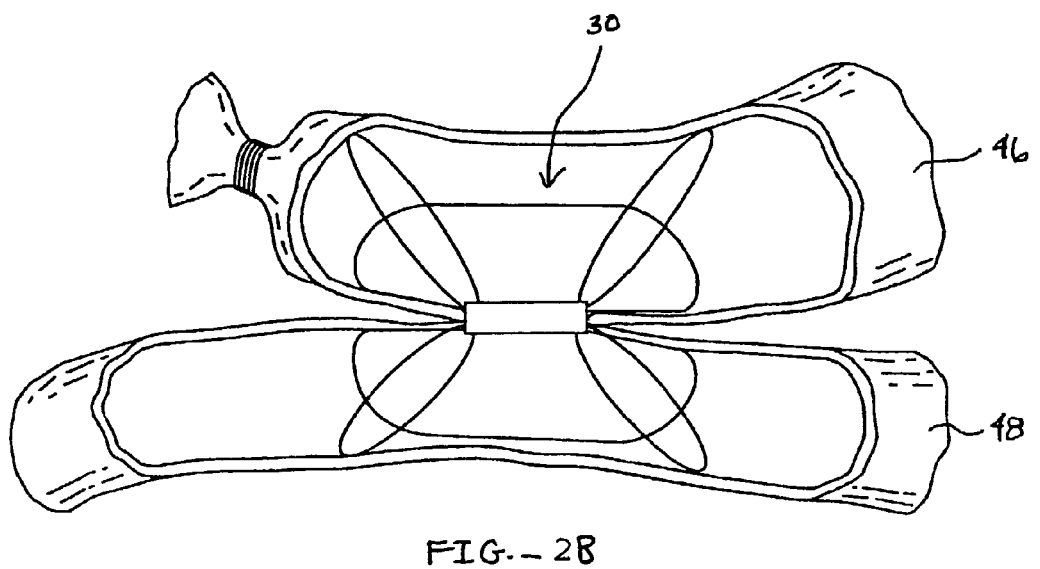
FIG.—2B

DEVICES AND METHODS FOR INTERCONNECTING VESSELS

CROSS-REFERENCE TO RELATED APPLICATIONS

Pursuant to 35 U.S.C. §119 (e), this application claims priority to the filing date of the U.S. Provisional Patent Application Ser. No. 60/327,126 filed Oct. 3, 2001; the disclosure of which is herein incorporated by reference

FIELD OF THE INVENTION

The field of this invention is anastomosis and anastomotic devices.

BACKGROUND OF THE INVENTION

The human body has numerous vessels carrying fluid to essential tissues and areas for circulation or excretion. When vessels become damaged, severed or wholly occluded due to physiological problems or diseases, certain sections must be bypassed to allow for the free and continuous flow of fluids. Anastomosis is performed for the purpose of connecting different conduits together to optimize or redirect flow around a damaged or occluded portion of a vessel.

In the context of the peripheral vascular and /or the cardiovascular system, atherosclerosis, a common vascular disease, can cause partial blockage or complete occlusion of an arterial vessel, resulting in restricted blood flow and therefore compromised perfusion to the tissue served by the blood flow. In the case of an occluded coronary vessel, for example, an area of the heart's myocardium would be compromised, which can lead to a myocardial infarction, or other ischemic heart syndrome such as congestive heart failure. In the case of peripheral vascular athersclerotic disease, occluded vessels lead to ischemic syndromes such as threatened limbs, stroke and other morbidities. Many cases, such a blockage or restriction in the blood flow leading to the heart or peripheral vessels can be treated by a surgical procedure known as an artery bypass graft procedure. A bypass procedure involves the establishment of an alternate blood supply path to bypass a diseased section of a diseased or compromised artery. In the bypass procedure, the surgeon typically dissects one end of a source or 'pedicled' artery (such as the internal mammary artery in the case of coronary artery bypass), or a free vessel segment (typically the saphenous vein in the leg), to use as a graft conduit to bypass the obstruction in the affected artery to restore normal blood flow. The graft vessel is connected to the obstructed vessel by means of an anastomosis procedure wherein an opening in the graft vessel is sutured to the obstructed vessel at an arteriotomy site made within the obstructed vessel. A side-to-side anastomosis procedure involves the attachment of two vessels at incised locations (e.g., arteriotomies) within a side wall of each of the vessels. An end-to-side anastomosis procedure involves the attachment of two vessels at an incised location within a side wall of one of the vessels and at the transected end of the other vessel. There are other indications for vessel anastomoses which include an alternative means of revascularizing diseased arteries by creating a side to side anastomosis between the distal end of the artery and an adjacent vein, thereby allowing the vein to become "arterialized" past the occlusion. Another indication includes the creation of an arterial to venous fistula for the purpose of either creating a dialysis access site, or, as an alternative means of creating arterial revascularization by "arterializing" a vein through creation of a conduit past the occlusive disease The patency of the anastomosis is crucial to a successful bypass, both by acute and long-term evaluation. Patency may be compromised by technical, biomechanical or pathophysiological means. Among the technical and biomechanical causes for compromised patency (also termed restenosis) is poorly achieved anastomoses, whether induced by poor placement, trauma at the anastomosis site or biological responses to the anastomosis itself. Improperly anastomosed vessels may lead to leakage, create thrombus and/or lead to further stenosis at the communication site, possibly requiring re-operation and further increasing the risk of stroke. As such, forming the anastomosis is the most critical procedure in bypass surgery, requiring precision and accuracy on the part of the surgeon. The current gold standard for forming the anastomosis is by means of suturing openings (natural or artificial) in the vessels together. Surgeons must delicately sew the vessels together being careful not to suture too tightly so as to tear the delicate tissue, thereby injuring the vessel which may then result in poor patency of the anastomosis. On the other hand, surgeons sometimes inadvertently suture too loosely or do not properly place the sutures so as to provide continuous seal around the arteriotomy site, resulting in leakage of fluid from the anastomosis. In addition to creating a surgical field in which it is difficult to see, leakage of fluid from the anastomosis can cause serious drops in blood pressure, acute or chronic. The loss of blood may cause other deleterious effects on the patient's hemodynamics that may even endanger the patient's life. In addition to the inherent inconsistencies in suture tightness, placement and stitch size and the lack of reproducibility, suturing an anastomosis can be very time consuming.

Advances in anastomotic instruments have been devised in the attempt to provide greater reproducibility of a precise anastomosis and to reduce the time that is required to complete an anastomosis and the necessary size of the surgical field. Many of these new instruments are stapling devices which deploy one or more staples at the anastomotic site in a single-motion action. While stapling techniques have been found to be successful in gastrointestinal procedures, due to the large size and durability of the vessels, it is less adequate for use in vascular anastomosis where the vessels are much smaller.

The manufacturing of stapling instruments small enough to be useful for anastomosing smaller vessels, such as coronary arteries, is very difficult and expensive. As stapling instruments are typically made of at least some rigid and fixed components, a stapler of one size will not necessarily work with multiple sizes of vessels. This requires a surgeon to have on hand at least several stapling instruments of varying sizes. This may significantly raise the cost of the equipment and ultimately the cost of the procedure.

Stapling instruments and staples which are adapted to conform to the smaller sized vessels are difficult to maneuver and, thus, a great deal of time, precision, and fine movement is necessary to successfully approximate the vessel tissue. Often stapling or similar coupling devices require the eversion of the vessel walls to provide intima-to-intima contact between the anastomosed vessels. Everting may not always be practical especially for smaller arteries because of the likelihood of tearing when everted. Another factor which may lead to damage or laceration of the vessel and/or leakage at the anastomosis site is the variability of the force that a surgeon may use to fire a stapling instrument causing the possible over- or under-stapling of a vessel. Still other factors include the unintended inversion of the vessel edges and the spacing between staple points. Rectifying a poorly stapled anastomosis is itself a complicated, time-consuming process which can further damage a vessel.

The tension and/or compression forces exerted on the vessel walls as a result of suturing and stapling can result in damage to the vessel wall, even to the extent of causing tissue necrosis. Damage to the intima of a vessel is particularly problematic as it may inhibit the natural bonding process that occurs between the anastomized vessels and which is necessary for sufficient patency. Furthermore, damaged vessel walls are likely to have protuberances that when exposed to the bloodstream could obstruct blood flow or may produce turbulence which can lead to formation of thrombus, stenosis and possible occlusion of the artery.

As cardiac surgery is moving into less invasive procedures, surgical access is being reduced, forcing surgeons to work in constantly smaller surgical fields. These procedures are made more difficult due to the multiple characteristics that are unique to each anastomosis and to each patient. For example, the arteries' internal diameter dimensions are difficult to predict and the inside walls are often covered with deposits of stenotic plaque which creates the risk of dislodging plaque into the patient's blood stream during the anastomosis procedure. The resulting emboli in turn create a greater risk of stroke for the patient. The dislodgement of plaque is most likely to occur when the vessel wall undergoes trauma such as the puncturing, compression and tension exerted on the vessel by suturing and stapling. The vessel walls can also be friable and easy to tear, and are often covered with layers of fat and/or are deeply seated in the myocardium, adding to the difficulty of effectively and safely performing conventional anastomotic procedures.

Accordingly, there is a need for an easier, safer and more efficient means for forming anastomotic communications which requires less time, reduces the risk of improper alignment, leakage, tearing and damage at the anastomosis site, and reduces the access space necessary for performing an anastomosis, and thereby accommodating minimally invasive surgical or interventional approaches.

Relevant Literature

U.S. Patents of interest include: U.S. Pat. Nos. 6,113,612; 6,113,611; 6,090,136; 6,068,656; 6,068,637; 6,063,114; 6,056,762; 6,036,704; 6,036,703; 6,036,702; 6,030,392; 6,026,814; 6,007,576; 6,007,544; 6,001,123; 5,961,545; 5,948,018; 5,921,995; 5,916,226; 5,904,697; and 4,214,586. Also of interest are the following PCT publications: WO 00/24339; WO 99/65409; WO 99/48427; WO 99/45852; WO 99/08603; WO 98/52474; WO 98/40036; WO 97/31591 and WO 97/31590.

SUMMARY OF THE INVENTION

The present invention provides implantable devices and associated methods for interconnecting human vessels, lumens, ducts or other tubular organs rapidly, safely and in a minimally invasive manner. These device and methods are particularly helpful in surgical procedures involving the anastomosis of small vessels or the like within a limited surgical access field, such as coronary artery bypass graft procedures (CABG), and such devices and methods are exemplary described in detailed herein in the context of a CABG procedure. As such, a subject device is positioned within a target or native vessel, such as downstream of a diseased coronary artery, which allows the attachment of a second, graft vessel to form the anastomosis. The subject invention provides devices and methods for forming both side-to-side and end-to-side anastomosis as well as kits including the subject devices for practicing the subject methods.

The devices of the present invention are for interconnecting conduits of a subject or patient, wherein at least a portion of the device is implantable within a conduit through an opening made within the conduit, includes a vessel connection member and a support mechanism operatively attached to the vessel connection member.

The vessel connection member provides a pathway for the transport of substances between the conduits. In certain variations of the subject devices, the vessel connection member has an annular configuration which may have a specific shape and dimensions, e.g., a diameter, substantially similar to the conduit opening, and, e.g., a height, sufficient to accommodate the thickness of the conduits' walls when appositioned against each other.

The support mechanism is configured to self-adjust to an inner dimension, such as the diameter, of a conduit to provide support about the opening of the conduit and to provide stability to the transport pathway established by the vessel connection member. The support mechanism is made of a flexible material, preferably having elastic properties to provide a constant outward force toward the vessel walls. In some situations with compliant vessels with high pressures, such as arteries, it is preferred that the support mechanism is dynamically responsive to the inner wall diameter of the vessel during normal physiological pressures, such as pulsatile blood pressure. Such flexible, elastic material is formed into a structure having an original or high profile configuration which is compressible or deformable into a lower-profile configuration, e.g., in order to fit through an opening in the vessel upon implantation or to fit into a delivery mechanism for delivery to an implant site within the vessel. In many embodiments, the support mechanism has an annular configuration wherein its self-adjustment and dynamic responsiveness, once implanted within a vessel, may involve radial and/or axial (or longitudinal) movement with respect to the vessel in attempting to achieve its original configuration. In other words, the annular support mechanism may, in certain embodiments, be configured to increase in a radial direction (with respect to the diameter of the vessel) while decrease in an axial direction (with respect to the longitudinal axis of the vessel). The support mechanism thus may be designed to provide both radial and axial stabilization of the vessel segment for anastomosis. The support mechanism may additionally be configured, or otherwise implanted in a particular juxtaposition within the vessel such that self-adjustment of the support mechanism further includes adjusting angularly with respect to the axis of the vessel. In other words, in a fully uncompressed state within the vessel, the structure of the support mechanism may lie at an angle with respect to the longitudinal axis of the vessel.

In certain variations of the subject devices, the support mechanism includes one or more support members attached to an edge of the vessel connection member. In a preferred embodiment, the support mechanism includes two flexible support members at substantially diametric locations about the transport pathway so as to straddle the pathway opening. The flexibility of the support members allows the support members to optimally adjust in size, shape and alignment with respect to a particular conduit to provide optimal support, regardless of the size and shape of that conduit. In certain variations of the support members, a support member, e.g., the plane defined by the support member, aligns at an optimal angle with respect to the internal conduit wall to provide an optimal force against the internal wall, i.e., strong enough to provide the necessary support but not so strong to deform the natural passage of the conduit wall, thereby avoiding the potential for stenotic formation about the support members. The support members may be comprised of a flexible material in the form of, e.g., wire microfilaments, bands or ribbons, etc. having loop or coil configurations or the like.

In certain device embodiments, the devices further include a sealing member operatively attached about a peripheral edge of the vessel connection member. When operatively implanted in a conduit, the sealing member utilizes the internal conduit pressure exerted thereon to form a substantially fluid-tight seal with the inner surface of the conduit whereby substances within the conduit are prevented from leaking from the conduit opening under normal physiological conditions. The sealing member may take the form of a flange or skirt having dimensions, e.g., diameter and surface area, selected according to the size of the conduit and to the size of the opening within the conduit. The sealing member may also take the form of an adhesive, collagen or other biomaterial.

In side-to-side embodiments of the present invention, a device may have a support mechanism and/or sealing member on each end or edge of a vessel connection member for insertion into openings in the side walls of the respective conduits. In end-to-side embodiments of the present invention, a device may have a support mechanism and/or sealing member on one end or edge of a vessel connection member for insertion into an opening in a side wall of one conduit and may have a vessel connection member having an extended height or a tubular extension member attached thereto to for insertion into an end opening within the other conduit. The vessel connection member or tubular extension member in the end-to-side embodiments may be positioned at an angle with the respect to the remainder of the device, the angle being selected to optimally accommodate a particular angle at which the conduits are to be interconnected with respect to each other.

The present invention includes methods of interconnecting a first and a second conduit in a patient including the steps of providing a device including a vessel connection member having first and second ends and a support mechanism operatively attached to the first end of the vessel connection member, reducing a dimension of the support mechanism, inserting the support mechanism into an opening of the first vessel, wherein upon being inserted into the first conduit, the dimensionally reduced support mechanism is allowed to optimally adjust in size and shape to an inner dimension, such as the diameter, and optimally positions itself with respect to an inner surface of the first conduit to provide support to the conduit and about the opening of the conduit. The methods further include inserting the second end into an opening in the second conduit, thereby establishing a pathway for the transport of substances between the two conduits.

Certain methods of the present invention providing the above described device further including a sealing member operatively attached about a peripheral edge of the vessel connection member, reducing a dimension of said sealing member, and inserting the dimensionally reduced sealing member into the opening in the first conduit, wherein upon being inserted into the first conduit, the dimensionally reduced sealing member is allowed to conform to an inner surface of the first conduit.

In methods for forming side-to-side connections between conduits, the device utilized may have a second support mechanism and/or second sealing member on the second end or edge of the vessel connection member, wherein the method further includes reducing a dimension of the second support mechanism and the second sealing mechanism and inserting them, respectively, into the opening in the second conduit.

In methods for forming end-to-side connections between conduits, the device may have a vessel connection member having an extended height or a tubular extension member attached thereto, wherein the method further includes inserting the vessel connection member into an end opening within the second conduit.

Thus, an object of the invention is to provide a device for interconnecting two vessels within a patient—which device is configured so as to be easily inserted into an opening in a vessel and remain without suturing or stapling at the anastomosis site.

Another object of the invention is to provide for a method of quickly and efficiently performing an anastomosis.

Another object of the present invention is to provide anastomotic devices and methods which minimize tension and compression forces at the site of the anastomosis.

Another feature of the invention is that the device is flexible and readily conforms to the inside wall of the native vessels to minimize flow resistance within the vessel and to reduce the risk of embolization.

Another object of the present invention is to provide an anastomotic device whose primary means of sealing to the vessel is by the device's ability to conform to the inside vessel wall.

Another feature of the invention is that one device can be used to accommodate a wide range of different size vessels.

Another aspect of the invention is that it can be used with a variety of conduits, vascular grafts; autologous, donor, artificial or prosthetic. Examples of vascular grafts include but are not limited to mammary, radial, gastroeiploic arteries to coronary artery, coronary artery to the coronary vein, saphenous vein to the coronary artery, arterial or venous arteries to the ascending or descending aorta, femoro-popliteal or other vessels (human, synthetic or tissue engineered) for lower limb bypass, and radial artery to vein for dialysis graft formation, etc.

These and other objects, aspects, advantages and features of the invention will become apparent to those skilled in the art upon reading this disclosure in combination with the accompanying figures.

BRIEF DESCRIPTION OF THE DRAWINGS

FIG. 1A is a view of a side-to-side embodiment of the invention having loop support members;

FIGS. 1B-D are schematic illustrations showing several possible orientations of the loop support members of the embodiment of FIG. 1A when operatively inserted within two vessels.

FIG. 2A shows an alternative side-to-side embodiment of the invention having loop support members and sealing members;

FIG. 2B shows the embodiment of FIG. 2A inserted within two vessels thereby interconnecting those vessels.

DETAILED DESCRIPTION OF THE SPECIFIC EMBODIMENTS

Figure 1E:
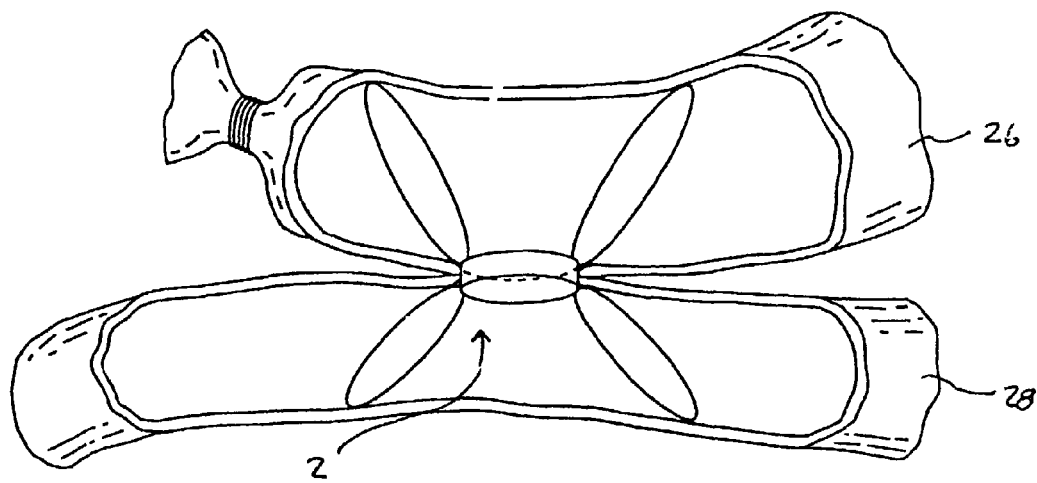
FIG. 1E shows the embodiment of FIG. 1A operatively inserted within two vessels thereby interconnecting those vessels.

The present invention provides implantable devices and associated methods for interconnecting human vessels, lumens, ducts or other tubular organs rapidly, safely and in a minimally invasive manner. These device and methods are particularly helpful in surgical procedures involving the anastomosis of small vessels or the like within a limited surgical access field, such as coronary artery bypass graft procedures (CABG), and such devices and methods are exemplary described in detailed herein in the context of a CABG procedure. As such, a subject device is positioned within a target or native vessel, such as downstream of a diseased coronary artery, which allows the attachment of a second, graft vessel to form the anastomosis. The subject invention provides devices and methods for forming both side-to-side and end-to-side anastomosis.

Before the present invention, devices and methods used therein are disclosed and described, it is to be understood that this invention is not limited to the particular components, devices or steps illustrated and discussed, as such may, of course, vary. For example, the devices of the invention and use of these devices is primarily described in the context of CABG procedures; however, the invention is useful for many other medical procedures for the communication of other natural and synthetic lumens and organs. Some of these other procedures include general vascular reconstruction and cerebral spinal fluid shunting for the treatment of hydrocephalus. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in communication with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

In further describing the subject invention, the devices themselves are first described in greater detail, followed by a review of various representative anastomotic methods in which the devices may be employed and a description of the kits of the subject invention.

Devices

The subject devices function to interconnect two vessels, to support those vessels and to seal them together to create a fluid tight communication between them, i.e., an anastomosis. Common to all of the devices of the present invention is the presence of a support mechanism attached to a vessel connector or connection member, often referred to as a "stoma," which provides a fluid communication passage or flow opening between two vessels.

Vessel Connector

The vessel connector or connection member or stoma, also referred to as a fluid communication member or fluid transport pathway, when operatively engaged with two anastomosed vessels, defines a passage or an opening through which fluid or other substances may flow between the vessels. More specifically, the opening of the connection member is aligned with, and may be partially inserted within, an opening, e.g., an arteriotomy, made within a side wall of a native or graft vessel or within a dissected end of a graft vessel or both, so as to provide a fluid passage or opening between the vessel lumens when the vessels are anastomotically connected with the subject devices operatively positioned within the vessel(s). The vessel connector provides a pathway through which fluid can be transported between the anastomosed vessels. More specifically, the connection member provides a location of permanent communication between the two sides of the anastomosis device and, thus, establishes fluid communication between the vessels connected by the implanted device.

The flow passage or opening may have varying shapes and sizes according to the size and shape of the arteriotomy and the application in which it is being used. As such, the connector preferably has a size, e.g., diameter or width, which can be accommodated within or by such openings and a shape which is annular, e.g., circular, oblong, elliptical, etc., but may have a non-annular shape instead.

The diameter of the flow opening of the connector (and tubular extension member depending on the particular embodiment, discussed in detail below) generally approximates the diameter of at least one of the vessels being joined by the device. As such, the diameter of the flow opening is typically from about 1.5 to about 5 mm for use with smaller vessels, e.g., coronary arteries, and is typically from about 1 mm or longer, but generally does not exceed about 20 mm for use with larger vessels, e.g., intestines. A connector in the form of an ellipse has a stoma whose minor or short axis may conform to the specifications for the diameter of the vessel into which it is connected and whose major or long axis is typically at least about 1 to about 5 times the length of the short axis.

The height dimension of the connector or stoma may also vary depending on the distance between the vessels' respective attachment points. The vessel connector or stoma has a height to accommodate the thickness of the wall of both the vessels when operatively connected to each other such that the edge of one vessel is aligned and in close apposition to the edge of the second vessel. As such, a short path for fluid communication and a fluid tight bond is formed between the edges to provide a patent anastomosis. Some embodiments have flow openings that define a tubular pathway or channel between the interconnected vessels. Other embodiments incorporate additional features to aid the formation of a fluid tight bond to prevent leakage.

A suitable height for the stoma may generally be determined as being about ⅓ to about 2 times the diameter of one of the vessels, e.g., the native vessel, into which it is inserted. As such, the length of the stoma may be as long as about 10 mm or longer for large vessels, e.g., intestines, and generally does not exceed about 3 mm for smaller vessels, such as coronary arteries.

The annular wall of the stoma may have a tapered or inset waist to provide a radius of curvature selected to optimize the appositioning of the incised edges of the two vessels to be anastomosed. Such a configuration also minimizes turbulence of the fluid flow from one vessel into the connection member and from the connection member into the second vessel.

The fluid communication passage or stoma may be made of a flexible, semi-flexible, semi-rigid or rigid material formed of a fluid-impermeable, blood-compatible metals including, but not limited to, surgical grade stainless steel, titanium and nitinol alloys, as well as blood-compatible polymers including, but not limited to, polyurethane, silicone rubber, polytetrafluoroetheylene, polyethylene, polypropylene and their respective copolymers. The stoma may comprise biodegradable materials such that the connector would degrade by the body's natural physiological processes after sufficient time has elapsed to allow the native tissues to heal around the anastomosis site.

The fluid communication passage or stoma may be comprised of multiple elements such as reinforcing components to provide crush-resistance or spring-like components to allow for folding and deformation during delivery of the device, but allowing the passage to return to its original shape after delivery. The passage or stoma may be formed of a single piece or at least two pieces. With a two-piece configuration, each piece is operatively engagable with one of the two vessels to be connected. The two pieces are then subsequently attachable to each other to form a leak-free fluid connection between the vessels. The two pieces may interconnect with each other by means of a simple interface connection means such as interference fit members, interconnecting clip members and hook-and-loop materials or may incorporate a mechanical component to provide a latching function. In one particular embodiment of the stoma, a two-piece configuration may be used which also traps at least a portion of the edges of the vessel openings to aid mechanical stability and sealing. For example, an interference fit or mechanical coupling may be designed to compress the edges of the vessels between the connector. Alternatively, one or several hooks could be incorporated on the outer surface of the stoma to penetrate and secure the vessel edges. Such mechanical attachment of the vessels to the stoma may also be performed on each vessel prior to connection of the two stoma pieces.

The fluid connection passage or stoma may also incorporate features which provide mechanical support of the vessel opening from outside the vessel. One embodiment includes the use of a small flange on the outer diameter of the stoma to provide an extravascular sealing surface for the edges of the vessel opening. In another embodiment, an elastically compressable washer may be incorporated on the external diameter of the stoma to provide an external sealing force against the vessel opening. Such extravascular sealing components may also comprise hemostatic materials such as collagen fibers or fibrin sealants to promote a fluid-tight seal.

Support Mechanism

The support mechanism of the subject devices is operatively attached to the vessel connector or fluid communication passage and is configured to be positioned within and to conform to at least a portion of an inner surface or circumference of a vessel into which it is to be delivered. The support mechanism is made of a flexible material, preferably having elastic properties to provide a constant outward force toward the vessel walls. In some embodiments, the support mechanisms are dynamically responsive to the inner wall diameter of the vessel during normal physiological pressures. Such flexible, elastic material is formed into a structure having an original or high profile configuration which is compressible or deformable into a lower-profile configuration, e.g., in order to fit through an opening in the vessel upon implantation or to fit into a delivery mechanism for delivery to an implant site within the vessel.

In many embodiments, the support mechanism has an annular configuration wherein its self-adjustment and dynamic responsiveness, once implanted within a vessel, may involve radial and/or axial (or longitudinal) movement with respect to the vessel in attempting to achieve its original configuration. An angular configuration of the support mechanism relative to the axis of the vessel allows for both radial and longitudinal forces to be transferred to the vessel walls to stabilize the vessel section. In other words, the annular support mechanism may, in certain embodiments, be configured to increase in a radial direction (with respect to the diameter of the vessel) while decrease in an axial direction (with respect to the longitudinal axis of the vessel). The support mechanism may additionally be configured, or otherwise implanted in a particular juxtaposition within the vessel such that self-adjustment of the support mechanism further includes adjusting angularly with respect to the axis of the vessel. In other words, in a fully uncompressed state within the vessel, the structure of the support mechanism may lie at an angle with respect to the longitudinal axis of the vessel The support mechanism includes at least one support member, and more commonly, a pair of support members, which are self-adjusting and responsive with respect to the size and shape of the vessel into which they are implanted. As such, the subject devices are easily self-retained within the vessel, optimally positioning the stoma relative to the arteriotomy site within a vessel, provide sufficient stability to the vessel walls adjacent the anastomotic site during and after the anastomotic procedure, and are prevented from displacing from their intended location once properly seated within the vessel.

In many embodiments, the support member(s) are configured to have a spring-like tension or memory so as to provide an original state which may also be described as a relaxed or high profile state by which it supports the vessel when operatively positioned within the vessel. The support member(s) may also have a compressed or deformed or low profile state which facilitates delivery of the subject devices to within a vessel. The support members are flexible enough to be compressed for delivery to a target site within a vessel and have enough spring tension or memory to attempt to return to their original state, thereby acting to conform to or press against the interior walls of the target vessel and fixing the subject device in place. The support members preferably conformingly contact the vessel walls upon expansion, with minimal extension into the flow path of the vessel so as to minimize disruption of the flow path.

In order to provide such performance characteristics, the support members are preferably made of a flexible, biocompatible material such as a metal including, but not limited to, stainless steel, titanium and nitinol alloys or other memory metals. High modulus polymers including, but not limited to, nylon, polyethylene, polypropylene or the like, are also suitable materials. In certain embodiments, the support members may also be made of a biodegradable or bioresorbable material. In many embodiments such flexible material is in the form of a wire, monofilament, band or ribbon in the form of a single loop, multiple loops, wound coils or similar structures which are able to abut against and adapt to the inner wall and annular configuration of the vessel. As such, the support members act to support the vessel wall and stabilize the fluid communication passage established between two vessels. The support members may be planar or may be angulated or bent in a manner to aid in deliverability and in-situ stability.

The support members may be made from flexible wire or monofilament having a diameter (thickness) in the range from about of 25 to about 300 microns, typically from about 50 to about 250 microns and more typically in the range from about 100 to about 200 microns. In another embodiment, the support members may be made from ribbon or flat stock material having a thickness in the range from about 25 to about 300 microns, typically from 50 to about 250 microns and more typically in the range from about 100 to about 200 microns, and having a width dimension in the range from about 25 to about 1000 microns, typically from about 100 to about 750 microns and more typically in the range from about 150 to about 500 microns.

In one embodiment, support members are fabricated from superelastic nickel titanium (Nitinol) wire of about 100 microns diameter. A Nitinol wire with suitable Active Austenite Finish (Af) to impart superelastic properties at both room and physiological temperature is selected, typically with an Af in the range of about 0 to about 20 degrees centigrade. The wire is wrapped around a supporting fixture maintaining an elliptical shape to the wire, and then fixed in place on the fixture. The wire being held in the correct configuration is fired in a furnace and subsequently quenched in cold water and the formed support member removed. The support member now maintains an uncompressed elliptical aspect. Other suitable and known methods may alternatively be used to form the support members of the present invention.

Each support member preferably has a diametrical or circumferential dimension such that it is able to adjust to the size or the internal diameter and circumference of the vessel into which it is placed. As such, support members having annular configurations, e.g., circular, oval or elliptical shapes will maximize adaptation to the interior of the vessel. The circumference, for example, of the support members in an original state is in the range from about 3 to about 60 mm typically from about 5 to about 40 mm and more typically from about 6 to about 30 mm. The diameter of a circular support member and the diameter along the major or long axis of an oval or elliptical support member, for example, in an original state is in the range from about 1 to about 20 mm typically from about 1.5 to about 12 mm and more typically from about 2 to about 9 mm. The diameter along the major or long axis of an oval or elliptical support member in an original state is in the range from about 1 to about 30 mm typically from about 1.5 to about 24 mm and more typically from about 2 to about 11 mm. The diameter along the minor or short axis of an oval or elliptical support member in an original state is in the range from about 1 to about 20 mm, typically from about 1.5 to about 12 mm and more typically from about 2 to about 9 mm.

Such diameter ranges of the support members may change when in a compressed state within the vessel, depending on the size of the vessel relative to the diameter. For example, the length of the major axis of a support member in a compressed state is likely to be shorter when within a vessel having a larger inner diameter than within a vessel having a smaller inner diameter, while the length of the minor axis of the same compressed support member is likely to be longer when within a vessel having a larger inner diameter than within a vessel having a smaller inner diameter.

Those embodiments of the subject devices having a plurality of support members may have support members of varying sizes, selected to optimally fit and support the vessel into which the support members are to be positioned. For example, a subject anastomotic device having two pairs of support members may have one pair of support members of one size and the other pair of another size. Additionally, paired support members may differ in size from each other.

In addition to the structure of the support members being flexible and compressible, the support members are flexible or movable with respect to the communication member. The support members are physically attached to the communication member or stoma by means of being imbedded into or attached to the stoma during the manufacturing process. The support members are attached at an angle with respect to the central axis of the connector in the range from 0 to 90 degrees, typically at an angle from 25 to 75 degrees and more typically in a range from 30 to 60 degrees.

In one embodiment, the attachment point of the support member to the connector is flexible, allowing the support member to angularly adjust with respect to the interior of the vessel as well as with respect to the connection member or stoma. When used within a vessel having a larger inner diameter, the angle that is formed between the axis of the support member defined between the point of attachment of the support member to the stoma and the most distal point of contact between the support member and the inner vessel wall (e.g., the major axis of the support member) is greater than that which is formed when used with in a vessel having a smaller inner diameter. As such, the subject devices are able to fit into, adapt to and be accommodated within the vessel regardless of the particular circumferential or diametrical dimension of the support member. Such feature of the present invention advantageously allows a single device to be used with vessels of varying sizes, reduces the number of devices necessary to be stocked, eliminates the time spent for sizing prior to implantation, maximizes the efficiencies of manufacturing and thus reduces the cost of the subject devices.

The flexibility of and mechanical force provided by the support members of the present invention can be adjusted by their size, shape and material.

In a preferred embodiment of the invention, the subject device has a pair of support members attached at opposing points along an edge of the connection member so as to straddle the opening within the vessel in order to better distribute the force provided by the support members against the interior wall of a first vessel, e.g., a native vessel, and to hold open the vessel lumen at and adjacent to the point of connection to a second vessel, e.g., a natural or prosthetic graft vessel. Further, the support members are self-retaining within the vessel under a range of likely physiological conditions without the need for an ancillary fixation or retention device or component.

To form a side-to-side anastomosis, a second pair of support members are attached to the opposite side or edge of the connector to thereby be engagable with a second vessel (see FIG. 1E). To form an end-to-side anastomosis, a tubular shaped extension member extends from the side or edge of the connector opposite the support member pair wherein the open end of the second vessel can be placed or fitted over the tubular extension member (see FIG. 5B) and secured thereto by means of a cuff, stay or ligature placed around the outside of the second vessel.

Sealing Member

The devices of the present invention may further include a sealing member to form a substantially fluid-tight seal with an inner surface of the vessel whereby substances within the vessel are prevented from leaking from the opening, i.e., arteriotomy site or transected end, made within the vessel under normal physiological conditions. In certain embodiments, the sealing member is in the form of a flexible flange or skirt or membrane attached about the periphery of an edge of the connector and adapted to utilize the internal vessel pressure (i.e., the internal fluid pressure, e.g., blood pressure) exerted thereon.

The flange or skirt has a first surface, herein also referred to as the lumen-facing surface, configured to utilize the internal conduit pressure exerted thereon to form a substantially fluid-tight seal between its second surface and an inner surface of the conduit. The second surface, herein also referred to as the contact surface, is adapted to contact and form a substantially fluid-tight seal with an inner wall or circumference of the vessel.

The flanges or skirts are sufficiently flexible and compliant, as well as sufficiently stiff, for easy insertion into an incision made within each vessel. Upon release, each flange subsequently conforms to the interior walls of the respective vessel to provide a sealing contact along the contact surface of the flange. As such, at least a portion of the sealing flange is comprised of a flexible, compliant material to enhance conformity of the flange to the vessel wall. The compliant material may be easily constricted (such as by bending, folding, compressing or constricting) to a size sufficient to fit through the arteriotomy opening but which has a natural tendency to return to an original (i.e., an unbent, unfolded, unconstricted) configuration to readily seal to and conform with the inside vessel wall, and to be securely and permanently self-retained within the vessel upon implantation. In some embodiments, this tendency provides a spring-like force that assists in securing the flanges to the vessel wall. Thus, when operatively placed, the flange(s) are caused to press against at least a portion of the inside wall of the target vessel primarily by the pressure within the target vessel, for example, by the intravascular blood pressure in the context of a CABG procedure. More specifically, the pressure against the wall created by the intravascular fluid flow or blood pressure, which is typically in the range from about 60 to about 180 mm of Hg under normal conditions, secures each flange in a sealing engagement against the inside vessel wall. Thus, the contact and conformation of the flange to the vessel wall is accomplished without compressing, tensioning or puncturing the vessel wall, but rather, is passive in that no other mechanical (e.g., staples, sutures, etc.) or adhesive (e.g., a biological glue) means is necessary to be used for maintaining the sealed engagement of the flange. This sealing engagement prevents the leakage of fluid from the incision or arteriotomy within the vessel wall during the implantation of the device, as well as from the resulting anastomotic site after completion of the anastomosis procedure. The stable and leak-free positioning of the device enables the vessels, and more particularly their respective incised edges, to be accurately appositioned with respect to each other, thereby facilitating the natural tissue bonding between the two.

The configuration and dimensions of the flexible flanges of the subject devices are important for the devices to accomplish their intended purposes. More specifically, each flange has a thickness, surface area, length and width (or diameter) dimensions for optimizing insertability of the flange into the vessel, maximizing the sealability of the flange to the vessel wall and minimally interfering with fluid flow within the interconnected vessels. The flanges comprise relatively thin walls, thus minimally interfering with fluid flow within the interconnected vessels. The flanges may have one continuous thickness or may have varying thickness throughout its structure. In either case, the flanges have optimal thickness such that flanges are sufficiently compliant and flexible so as to be compressible for insertion into a vessel, while being sufficiently rigid to facilitate insertion without the flange folding on itself or becoming kinked or otherwise mechanically damaged upon entry into the vessel.

The thickness of the flange is generally in the range from about 100 to about 500 microns and preferably in the range from about 150 to about 400 microns. Exemplary width and length (or diameter) dimensions for these surface area ranges are generally from about 3 to about 15 mm for the width and from about 6 to about 30 mm for the length, and more typically from about 4 to about 9 mm for the width and from about 8 to about 15 mm for the length, depending on the exact size of the target vessel to be anastomosed.

The flanges have a surface contact area at least marginally greater than the surface area of the opening in the vessel through which the flange is inserted. For example, for devices suitable for use in CABG anastomosis procedures, the contact surface of a flange has a surface area that is generally in the range from at least about 20 $mm^2$, usually at least about 30 $mm^2$ and more usually at least about 50 $mm^2$, and usually no greater than about 450 $mm^2$ (such as for use in the aorta or other large lumen)

The sealing members may have a variety of different configurations, thickness, surface areas, lengths and widths (or diameters). Useful configurations include, but are not limited to, partial cylinders or generally planar configurations having circular, elliptical, biconvex, stared, pedaled or rectangular shapes, or combinations of these configurations, which are described in greater detail in co-pending U.S. patent application Ser. No. 09/771,007, which is herein incorporated by reference. Generally, the size and shape of the sealing members are dependent on the size (i.e., the circumference or diameter) and shape of the vessel opening into which it is to be used. For example, larger flanges may be preferable when performing a proximal anastomosis to an aorta, or when anastomosing peripheral (e.g., in the leg) or abdominal vessels while smaller flanges are more appropriate for coronary arteries and veins. Also, the length or width (diameter) dimensions or both, may be dictated by the length of the incision or arteriotomy within the lumen or vessel into which the flange is to be placed.

Suitable materials for the sealing members are biocompatible, and have appropriate mechanical properties for facilitating insertion, retention and sealing of the flanges within the vessels. Additionally, the biocompatible devices may be made of any suitable bioresorbable or biodegradable materials, as well as autologous, allo- and xeno-graft biomaterials. Bioresorbable materials of interest include, but are not limited to, degradable hydrogels, polymers such as polylactides/glycolides, polydioxanone, polytrimethycarbonate or polycarptolactone and their copolymers; protein cell matrices, plant, carbohydrate derivatives (sugars), and the like. Non-resorbable polymers and elastomers such as silicone rubbers, fluoropolymers, polyolephins or polyurethanes might also be used. Sealing members made from non-metallic materials may also include fiducial markers to assist in placement and assessment of the device in-situ by imaging means. Markers may include metallic or radiopaque fillers embedded within the material in the form of stripes or targets, and may be used for image guided surgical implantation of the device.

The sealing member may further include reinforcement portions integral with or embedded within the material of the flange to further reinforce the sealing force of the flanges against the vessel walls and acts to better support and stabilize the sealing members within the vessels into which they are implanted, thus, optimizing the overall stability of the device, once the anastomosis has been completed. The reinforcement portions may be made of the same or similar materials and may have the same or similar biocompatibility, sealing, insertion, compliance and tensile properties as the flanges. The reinforcement portions may have any suitable shape include circular, elliptical, rectangular or provide a ridge, e.g., in the form of a monofilament, within the flange.

In addition, the flanges of the present invention may be fabricated from composites of two or more different types of materials, etc., e.g., the device may be fabricated from a blood impermeable membrane attached to a structural article or tissue scaffold.

The sealing flange may be attached to the connection member independently of the support member(s) wherein the sealing flange may reside over the support member(s), e.g., outside the wire loops, or may reside within the support member (s), e.g., inside the wire loops such that at least a portion of the support member(s) wrap around the external surface of the sealing flange. Alternatively, the sealing flange may be fabricated with the support member(s), e.g., wire loops, embedded within the flange.

The side-to-side anastomotic devices of the subject invention include at least one sealing flange connected along the periphery of the connector. In many embodiments two sealing flanges are employed, each connected to a respective peripheral edge of the connector. The two flanges may have the same size and shape or may have different sizes (circumference, width or length) and shapes from each other. Different sizes are useful in situations where it is desirable to interconnect two vessels which are different in size.

The end-to-side anastomotic devices of the subject invention include a single or first flange as described above positioned at one end of a tubular extension member, where the tubular member and the first flange are connected by a the flow opening formed by the vessel connector in the manner described above with respect to the side-to-side device of the present invention. The tubular extension member may be normal to, or positioned at an angle relative to, the surface of the flange, as described and illustrated in co-pending U.S. patent application Ser. No. 09/771,007.

In other embodiments of the present invention, the sealing mechanism of the subject devices may be flangeless, and rather is an adhesive material or a structure that provides adhesion applied or attached to the subject devices. Such materials or structures include but are not limited to bioglues, collagen structures or other resorbable biologic adhesives.

The subject devices may be used to join any two (or more) vessels together such that fluid communication is established between the lumens of two joined vessels, where representative types of vessels include, but are not limited to, vascular vessels and other vessels of the body, where one of the vessels may be a synthetic vessel or graft vessel from a donor, e.g., autograft or allograft. While the specific embodiments described herein illustrate devices for joining only two vessels, those skilled in the art can appreciate that embodiments for joining three, or possibly four or more, vessels are possible under the present invention. Both side-to-side and end-to-side anastomotic devices are now separately described in greater detail below with the respect to the accompanying Figures.

Exemplary Side-to-Side Anastomotic Devices

Referring to FIGS. 1-3, there are shown various exemplary embodiments of side-to-side anastomotic devices of the present invention. FIG. 1 illustrates one embodiment of an anastomotic device 2 having a vessel connector or stoma 4. Connector 4 has an annular shape, having length and width (diameter) dimensions, discussed in detail above, and inset waist 5 which optimize placement and positioning of the edges of the openings made within the two vessels in a side-to-side arrangement.

Attached at opposing edges 6, 8, respectively, of connector 4 is a pair of support members 10*a*, 10*b* and 12*a*, 12*b*, each support member pair being insertable into a respective vessel. Each support member has a flexible loop configuration which has an original or unconstricted high profile state and is compressible or constrictable to a low profile state for insertion into an arteriotomy within the respective vessel. The size, e.g., circumference or diameter, of the loops may be selected within a certain range, e.g., 2 to 5 mm for coronary artery applications, for an optimal fit within the respective vessels; however, as mentioned above, the flexible construct of the support members is such that they are self-accommodating within the respective vessels regardless of the size of the support members. FIGS. 1B, 1C and 1D illustrate such feature of the subject devices.

When operatively positioned and in an original or high profile state within the respective vessels, as shown in FIGS. 1B, 1C, and 1D, each support member or loop 10*a*, 10*b*, 12*a*, and 12*b*, and more specifically the axis 13 (see loop 12*a* in each FIG.) defined by the point of attachment 7 between each loop and connector 4, defines an angle α with the vessel wall 15. The size, e.g., diameter, of loops 10*a*, 10*b*, 12*a*, and 12*b* relative to the diameter of the vessels 14, 16 dictates the magnitude of angle α. Thus, for a given size loop, angle α will be greater in larger vessels, such as vessels 14 and 16 of FIG. 1B and vessel 22 of FIG. 1D, than for smaller vessels, such as vessels 18 and 20 of FIG. 1C and vessel 24 of FIG. 1D. As illustrated in FIG. 1E, oftentimes, in CABG surgery for example, one vessel 26, i.e., the graft vessel, is larger than the other vessel 28, i.e., the native vessel and, as such, the loops of one loop pair will conform with and/or press against the internal vessel wall at a different angle α than the loops of the other loop pair. For most applications of the subject devices, angle α generally ranges from about 0° to about 90°, typically from about 15° to about 80°, and more typically from about 30° to about 70°.

Referring now to FIGS. 2A and 2B, there is shown another embodiment of the subject device. Anastomotic device 30 has connector 32 and loop support pairs 34*a, b* and 36*a, b* similar to that of device 2 of FIG. 1A. In addition, anastomotic device 30 has a first sealing flange 38 and a second sealing flange 40 attached at the periphery of opposing edges 42 and 44, respectively, of connector 32. As with their corresponding loop pairs, first and second flanges 38, 40 are flexible and compliant for easy insertion into an incision made within each vessel. FIG. 2B illustrates device 30 operatively implanted within two vessels 46, 48 in a side-to-side arrangement.

Figure 3A:
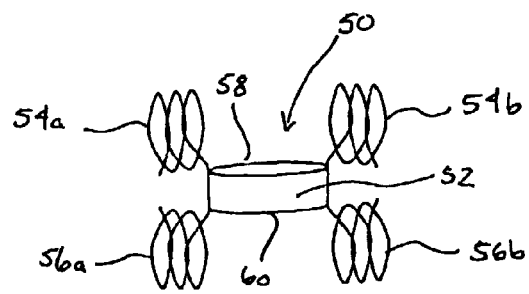
FIG. 3A is a view of a side-to-side embodiment of the invention having coil support members.
Figure 3B:
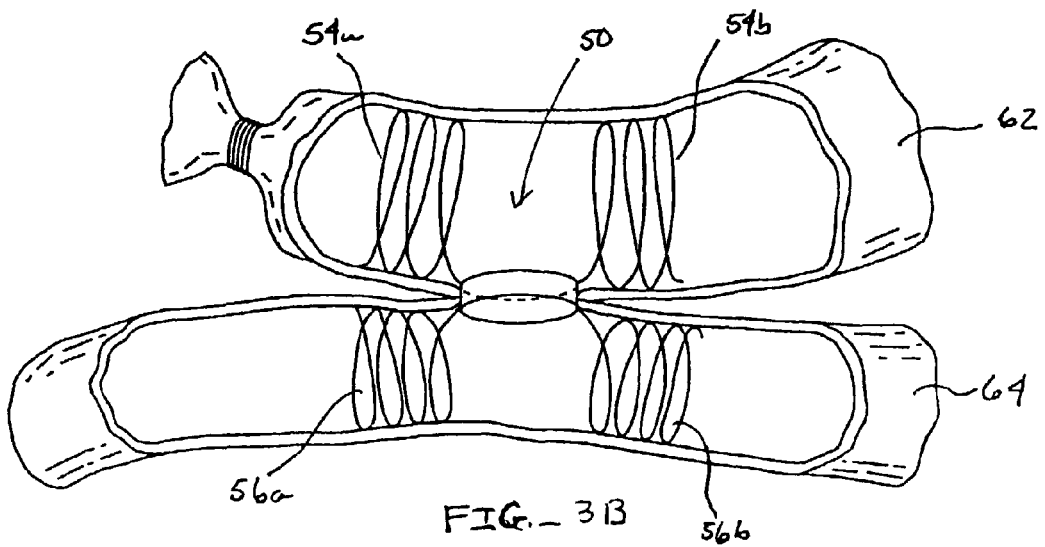
FIG. 3B shows the embodiment of FIG. 3A inserted within two vessels thereby interconnecting those vessels.

FIGS. 3A and 3B illustrate yet another side-to-side embodiment of the subject device. Anastomotic device 50 has connector 52 as described above with respect to the other embodiments, however, unlike the previous embodiments, the support members each have a coil configuration rather than a loop configuration. The support members are arranged in coil pairs 54*a, b* and 56*a, b* attached at opposing edges 58 and 60, respectively. The coils are compressible into a low profile state for insertion into a vessel and are subsequently relaxed upon release of the compression force into their original, high profile states to the extent permitted by the opposing force of the vessel walls. In their original state, each coil pair has coils having a central axis which are preferably aligned substantially co-axially with each other and, thus, substantially perpendicular to the central axis of the connector. Although not shown, anastomotic device 50 may further include one or more sealing flanges 38 as described above. FIG. 3B illustrates device 50 operatively implanted within two vessels 62, 64 in a side-to-side arrangement. As with the loop embodiments of the present invention, the coil embodiments of the support members are also self-adjusting and accommodating within the vessel into which they are implanted. As such, coil pair 54a, 54b unconstricts to a greater diameter within larger vessel 62 than do coil pair 56a, b within smaller vessel 64.

Exemplary End-to-Side Anastomotic Devices

Figure 4:
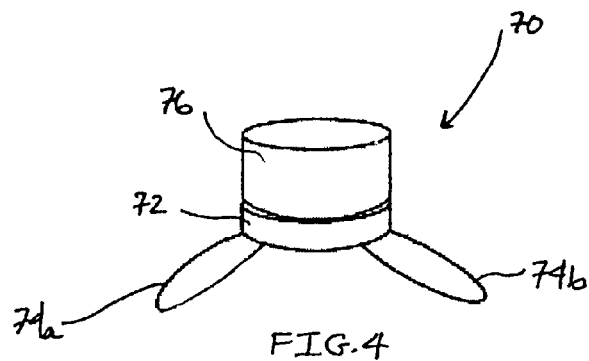
FIG. 4 is a view of an end-to-side embodiment of the invention having loop support members and a sealing member.
Figure 5A:
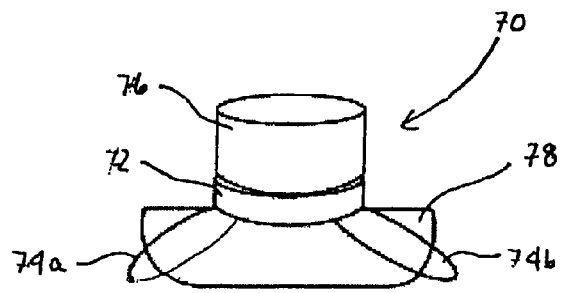
FIG. 5A is a view of another end-to-side embodiment of the invention having loop support members and a sealing member.
Figure 5B:
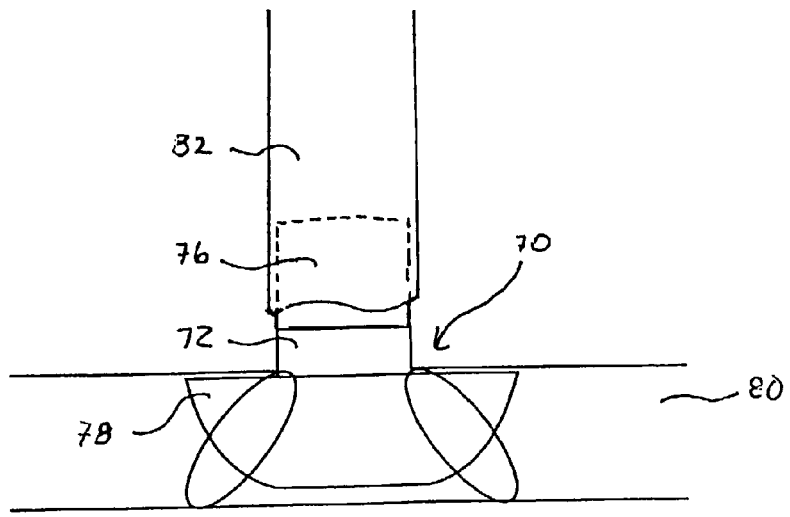
FIG. 5B shows the embodiment of FIG. 5A inserted within two vessels hereby interconnecting those vessels.

FIGS. 4, 5A and 5B illustrate various exemplary embodiments of end-to-side anastomotic devices of the present invention. In FIG. 4, end-to-side anastomotic device 70 has a connection member 72 and loop pair 74a, b similar to those connection members and loop pairs described above with respect to the side-to-side embodiments of the present invention. Device 70 further includes a tubular member 76 extending from the opposite edge of connection member 72 which is configured and sized to be positioned within the transected end of a vessel, i.e., a graft vessel. As mentioned above, tubular extension member 76 may be normal to, or positioned at an angle relative to, the surface of the flange. The length of tubular member 76 typically ranges from about 2 to about 10 mm. The outer diameter of tubular member 76 has a dimension that approximates the inner diameter of the graft vessel to be attached, and therefore is typically in the range from about 2 to about 12 mm, and more typically from about 3 to about 8 mm. Wall thickness of the tubular member typically ranges from about 10 to about 300 microns, and more typically from about 50 to about 200 microns. Tubular member 76 may be integrally formed with connection member 72 or may be a separate component which is attachable to connection member 72. Tubular member 76 may be made of the same or similar material as that of connection member 72 or flange 78.

FIG. 5A illustrates device 70 further including a sealing flange 78 as described above with respect to the side-to-side embodiments of the present invention. FIG. 5B illustrates device 70 of FIG. 5A operatively implanted within two vessels 80, 82 in an end-to-side arrangement. While loop pair 74a, b and flange 78 are insertable and accomodatable within vessel 80, i.e., a host vessel, as described above, tubular member 76 is inserted into the transected end of vessel 82, i.e., the graft vessel.

Materials in General

Those skilled in the art will recognize that certain materials are preferred in connection with certain uses of the invention. In general the material should be comprised of one or more materials which are biocompatible and non-toxic to the vessels into which they are inserted. In general the device is used for connecting vessels of the cardiovascular system and therefore should be comprised of a material which provides a high degree of hemocompatibility. The material should not prevent growth of a new intima layer. However the material may comprise antirestenosis or antiproliferative agents such as smooth muscle cell inhibitors, irradiants, thermal treatments, etc. The material used in the construction of the invented device should be designed to have thickness and properties appropriate for the stiffness and flexibility of the vessel into which the device is inserted. It should be noted that artery walls continuously dilate and contract due to the systole and diastole of the heart. If the device is too rigid the device can cause irritation and injury to the intima layer of the vessel. Accordingly, the device should be designed to avoid any inflammatory response or immune response that has adverse consequences. In addition to having the desired degree of flexibility and composition the device should be designed so that it does not present protrusions or disruptions to the flow of material through the vessels connected by the device. Interruption of flow can cause clots to form which could in certain circumstances be fatal to the patient.

Any or all of the different materials can be coated with a desired compound or drug. The device blood-contacting surfaces of the sealing members, connection member and extension member may be lined with endothelial cells. These cells may be cells extracted from the patient the device is being placed in or from a tissue culture of such cells from another patient. Further, the materials may be embedded with any desired compound or drug which provides desired properties to the device. Useful coatings include drugs such as heparin which may be used alone or in combination with hydrogels or hydrophilic compounds. Any anticoagulant compound may be extremely useful as a coating on devices inserted into the vessels of the cardiovascular system. Any anticoagulant compound may be extremely useful as a coating on devices inserted into the vessels of the cardiovascular system. Compounds such as Taxol may be useful for coating or embedding within materials of a device of the invention.

A device of the invention may be comprised of any material that is appropriate for localized delivery of various compounds including compounds such as antiplatelet agents, calcium agonists, antiinflammatory compounds, antiproleferative drugs, hypolipidemic agents, and angiogenic factors. The device may be comprised such that all or any of these compounds are coated on the surfaces of the device, embedded within it or incorporated within a chamber (not shown) of the device so that the compound is released in a metered fashion from the device to the area surrounding the anastomosis.

In certain preferred embodiments, the devices of the present invention are provided with a pre-attached graft vessel fabricated from synthetic or natural materials so as to form a bioprosthetic device. Suitable synthetic materials include Dacron, expanded PTFE, carbonaceous materials, such as carbon fibers, and other similar materials. Suitable natural tissues include autologous, allogenic or xenogenic tissue.

The bioprosthetic device may also be fabricated intraoperatively. The tissue may be any convenient tissue that is capable of providing the appropriate flexibility and rigidity to the final bioprosthetic device, e.g., after one or more processing or "fixing" steps, such that the device is capable of serving its intended purpose. In many embodiments, the tissue is collagenous in nature, by which is meant that a substantial component of the tissue is collagen. Tissues of interest include, but are not limited to: pericardium, connective tissues, e.g., dura matter, tendons, ligaments, skin patches, mucosal patches, omentum, arteries, veins and the like, where the tissue is generally mammalian in nature, where specific species of interest include cow, horse, pig, sheep, primates, e.g., monkeys, baboons, and humans, where in many embodiments, the tissue will be of human origin, e.g., where the tissue may be an auto- or allograft, e.g., from a live person or a cadaver. Following harvest of the suitable tissue, the tissue is cut or shaped to the desired configuration, where the tissue may be manually shaped or shaped at least partially with the help of specialized tools/machines, e.g., die cutting devices, etc. At some point during preparation, the tissue may be processed to provide for one or more desirable attributes, where processes of interest include cross-linking, immunogenicity minimization modification, e.g., by fixation, modification to reduce enzymatic attack, and the like. Representative bioprosthetic materials and methods for their manufacture which may be readily adapted by those of skill in the art to fabricate anastomotic devices according to the present invention are described in U.S. Pat. Nos. 6,106,555; 6,093,530; 6,008,292; 5,984,973; 5,855,617; 5,609,600; 5,595,571; and the like, the disclosures of which are herein incorporated by reference.

Anastomotic Methods

As indicated above, the methods of the subject invention may be employed to join any two or more vessels together and are particularly suited for joining vessels together that are located, or are to be located, in a living animal, e.g., the human body. The subject methods are particularly useful for joining vascular vessels, where any type of vascular vessel may be joined to another vessel, where representative types of vascular vessels include, but are not limited to: coronary vessels, peripheral vessels, neurovascular vessels, etc. As such, the subject methods can be used in a variety of applications, including coronary bypass applications, including both proximal and distal anastomoses, peripheral vascular bypass applications, neurovascular bypass applications, and the like. The vessels that are joined may be naturally occurring vessels, e.g., autologous donor to a graft, etc., or synthetic/fabricated vessels, e.g., synthetic vein, artery grafts, prosthetic tubes, etc. In those embodiments where the subject devices are intended to join vascular vessels together, e.g., human vascular vessels, they are dimensioned or shaped so as to work with the target vessels to be joined, e.g., they are shaped or dimensioned such that they fit within the human vessels, e.g., arteries, veins, to be joined.

The devices of the present invention may be inserted with or without the use of special surgical tools. The devices may be inserted or implanted using surgical tools or alternatively using a catheter designed specifically for the less invasive placement and release of the device within the vessels for intercommunication thereof. Such delivery and implantation tools are more fully described in co-pending U.S. patent application Ser. No. 09/771,007.

Alternatively, the device may be inserted manually (i.e., using the surgeon's fingers alone) or in combination with other surgical equipment normally used when operating on a patient. The subject methods may be performed intravascularly or extravascularly, i.e., an intravascular or extravascular approach may be employed with the subject devices. In intravascular methods, the device is delivered to the anastomotic site through a vessel, e.g., the donor or host vessel, where any convenient delivery means may be employed, including the delivery sheaths and devices described in co-pending U.S. patent application Ser. No. 09/771,007. For extravascular protocols, the device is introduced to the anastomotic site from outside of the vessel.

The present invention provides for the following general steps for interconnecting vessels using an anastomotic device of the present invention having a vessel connector and a support mechanism having at least one support member as described above. First, the profile or a dimension of the at least one support member, also referred to as a first support member, is reduced in size and then inserted into an opening of a first vessel. When released, the support member self-adjusts and dynamically converts to its original configuration and conforms to an inner surface or circumference of the vessel, wherein the vessel connector is aligned within the opening in the vessel. For those embodiments of the device having a second support member, such as where the support mechanism comprises a pair of support members, the second support member is inserted into the opening made in the first vessel and allowed to unconstrict and self-adjust to its high profile configuration. For those embodiments of the subject device further including a sealing flange, the flange is compressed or folded to a constricted, low profile state along with the support members and inserted through the openings and allowed to deploy in a manner that produces a sealing relationship between the upper surface of the flange and the inner wall of the vessel.

For side-to-side embodiments of the device, wherein the device has a second support mechanism or a second pair of support members, as described above, with or without a sealing flange, the steps just recited are repeated with respect to a second vessel having an opening therein.

For end-to-side embodiments of the device, the transected end of the second vessel is fitted over the end of the vessel connector without the support mechanism, and secured. In certain embodiments, the dimensions of the tubular member are slightly larger than the inner diameter of the graft vessel such that the open end of the graft vessel must be stretched to slide it over the tubular member and, upon release of the stretching force, constricts with sufficient force to secure it to the tubular member. In other embodiments, a securing means may be employed to secure the end of the graft vessel to the tubular member. Securing means of interest include bioglues, ties, loops, lashes or the like to secure the vessel to the tubular member. Other securing means includes sealing rings that can be slid over the graft vessel/tubular member structure followed by constriction to secure the vessel to the tubular member, or which move from a first expanded state to a second constricted position, such as those described in U.S. Pat. No. 6,056,762, the disclosure of which is herein incorporated by reference. Depending on the particular protocol employed, the tubular member of the device may or may not have been pre-secured to the open end of the graft vessel.

In the above-described methods, openings or slits are first prepared in the sides of the graft and host vessels. The openings or slits are sufficiently large to allow insertion of support members and sealing members in a constricted or bent configuration, but are small enough such that the support members and sealing members cannot readily be pulled out of the vessel through the opening upon deployment and provide a leak free seal around the openings or slits. In many embodiments, the openings will be slits ranging in length from about 2 to about 8 mm, usually from about 3 to about 6 mm.

As indicated above, any suitable delivery protocol may be employed. In communication with intravascular delivery of the device, it may be desirable to provide the device of the invention using a catheter or surgical dispenser through which the device is moved and inserted. Such delivery devices are disclosed in U.S. patent application Ser. No. 09/771,007.

It may also be necessary to utilize stay sutures to stabilize the graft near the heart. These sutures are placed through fat or tissue surrounding the vessel in order to provide additional stability to the anastomosis. This is normally done when grafting the internal mammary artery to the coronaries but may be necessary in some cases in order to prevent the vessels from being inadvertently separated from each other. Still, in certain embodiments, it may be desirable to employ a means for holding together the two vessels to be anastomosed during practice of the subject methods. A suitable holding means, i.e., proximator, appositioner, vessel stabilizer, etc., will comprise a means for holding the donor and graft vessels, e.g., the coronary artery and the IMA, together in a sufficiently close relationship, e.g., in adjacent relationship, so that the device can join the vessels as described above.

The above steps result in the establishment of fluid communication between the lumens of the host and graft vessels. After the device has been held in place for significant periods of time, the vessels will naturally develop a new intimal layer and fuse through normal wound healing. At this point the device may no longer be needed and could, if so designed, begin dissolving or surgically removed.

Stopped Heart/Beating Heart Procedures

The device of the present invention can be used for CABG or more specifically complete an anastomosis while the patient's heart is beating or after the patient's heart has been stopped. Beating heart procedures can be carried out by making a variety of different types of initial incisions which could include a sternotomy where the patient's sternum is bisected or by making smaller incisions and utilizing minimally invasive surgical devices and methods (see Benetti, F. in U.S. Pat. No. 5,888,247). After the necessary incisions are made the heart is stabilized using a stabilizer device. Thereafter the device of the invention is inserted as described above.

The device can also be used in a stopped heart situation. Many of the different types of initial incisions mentioned above or others can be used to access the patient's chest cavity. A suitable graft vessel is harvested from the patient. Thereafter the patient's heart is stopped using a suitable cardioplegia. Thereafter, the steps referred to above with respect to insertion of the device are carried out. Although the present invention can be used in communication with a stopped heart procedure one of the advantages of the present invention is the ease of manipulation of the device in order to carry out an anastomosis. Because of the simple efficient manner in which the device of the invention can be manipulated and inserted it can generally be carried out while the patient's heart is beating.

Robotic Assist Intervention

The device can be used when robotic assist devices are utilized by the surgical staff. Robotic assist device surgery is typically performed by the surgeon through the use of robotic arms. The use of the robotic arms scales the motion of the surgeon and filters out unwanted tremors. This allows the surgeons to perform the surgery through smaller incisions and in more constricted spaces. Examples of such systems are the ones marketed by Intuitive Surgical Systems as described in U.S. Pat. No. 5,855,583.

Surgical Access and Visualization

The device of the present invention can be used during hybrid procedures where surgical procedures are combined with interventional cardiology techniques. Such procedures use fluoroscopy to visualize and position the catheter delivery systems. The catheter is normally placed through femoral or radial access. Direct surgical access to the heart is typically achieved via small incisions in the chest or abdomen. A single or multiple trocar ports or a minimally invasive small retractor is placed in these incisions. An endoscope may be used to aid in visualization and/or deliver the catheter when employed to deliver the device. The device can also be used in complete percutaneous procedures where no direct access to the heart is available to the physicians.

Kits

Also provided are kits that at least include one device according to the subject invention, where in many embodiments the kits may include two or more devices having varying sizes and/or configurations of support and sealing members. The kits may further include other tools such as delivery devices, (e.g., a delivery catheter, loaded delivery device, etc.), proximator or sizing devices for determining the appropriate size of the device to be used, and the like, as described above, which devices find use in performing an anastomosis with the subject devices. The subject kits may also include securing or reinforcement means, e.g., biocompatible glues/adhesives, extravascular sealing components, etc.

Additionally, the subject kits typically include instructions for using the devices in methods according to the subject invention. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc.

It is evident from the above description and results that the subject invention provides important new anastomotic devices and procedures which overcome a number of disadvantages currently encountered in the field of anastomosis. The subject devices are easy to use and can provide for vessel joining with out the required use of sutures, staples, glues or other holding means. In addition, the subject devices are substantially atraumatic and provide for rapid healing. As such, the subject invention represents a significant contribution to the field.

The present invention is shown and described herein in what is considered to be the most practical, and preferred embodiments. It is recognized, however, that departures may be made there from, which are within the scope of the invention, and that obvious modifications will occur to one skilled in the art upon reading this disclosure.

What is claimed is:

1. A device for interconnecting first and second vessels, said device comprising:
    a vessel connection member comprising a fluid communication lumen extending therethrough between first and second openings formed, respectively, at first and second ends of said vessel connection member, wherein said first and second ends are each insertable into said first and second vessels, respectively; and
    first and second pairs of support members, each pair consisting of two single loops attached to substantially opposing sides of said first and second openings in said first and second ends of the vessel connection member, respectively, wherein each of the support members is sufficiently flexible so as to angularly adjust with respect to a longitudinal axis of said vessel connection member and to substantially conform to the inner surface of said vessels in which each of the support members are implanted to exert a force against the inner surface of the first vessel which fixes said device in an operative position relative to said vessels.

2. The device according to claim 1, further comprising:
    a first sealing member attached to at least one of an outer perimeter of said vessel connection member adjacent to said first opening so that, when in an operative position, said first sealing member forms a substantially fluid-tight seal around said first opening.

3. The device according to claim 2, wherein said first sealing member comprises at least one flexible flange.

4. The device of claim 1, wherein said support members are configured to self-adjust to the inner surface of said first vessel.

5. The device of claim 1, wherein said support members comprise shape memory material.

6. The device of claim 5, wherein said shape memory material comprises one of at least shape memory metal and high modulus polymers.

7. The device of claim 6, wherein said memory metal comprises one of at least stainless steel, titanium and Nitinol alloys.

8. The device of claim 6, wherein said high modulus polymers comprises one of at least nylon, polyethylene, and polypropylene.

9. The device of claim 1, wherein said support members are at least one of embedded within, attached directly to, and adhered to said vessel connection member.

10. The device of claim 1, wherein said support members are configured to change in both radial and axial directions with respect to said first vessel.

11. The device of claim 1, wherein said support members are formed integral to the vessel connection member.

12. The device of claim 1, wherein said support members are formed unitary to said vessel connection member.

13. The device of claim 1, further comprising:
a second sealing member attached to at least one of an outer perimeter of said vessel connection member adjacent to said second opening so that, when in an operative position, said second sealing member forms a substantially fluid-tight seal around said second opening.

14. A device for interconnecting first and second vessels, said device comprising:
a vessel connection member comprising first and second fluidically coupled openings formed, respectively, at first and second ends of said vessel connection member, wherein said first end is insertable into said first vessel; and
first and second support members each consisting of a single loop attached to said first end of said vessel connection member at substantially opposing sides of said first opening, wherein each of the support members is sufficiently flexible so as to angularly adjust with respect to a longitudinal axis of said vessel connection member and to substantially conform to the inner surface of said first vessel to exert a force against the inner surface of the first vessel which fixes the device in an operative position; and
a first sealing member attached to one of an outer perimeter of said vessel connection member adjacent to said first opening so that, when in an operative position, said first sealing member forms a substantially fluid-tight seal around said first opening.

15. The device according to claim 14, wherein said sealing member comprises a vessel-contacting surface and a lumen-facing surface, wherein, upon implantation of said first end into the first vessel, said vessel-contacting surface readily conforms to and seals against the inner surface of said vessel and wherein the lumen-facing surface utilizes internal vessel pressure exerted thereon to form said substantially fluid-tight seal.

16. The device of claim 14, wherein said support members are configured to self-adjust to the inner surface of said first vessel.

17. The device of claim 14, wherein said support members comprise shape memory material.

18. The device of claim 17, wherein said shape memory material comprises one of at least shape memory metal and high modulus polymers.

19. The device of claim 18, wherein said memory metal comprises one of at least stainless steel, titanium and Nitinol alloys.

20. The device of claim 18, wherein said high modulus polymers comprises one of at least nylon, polyethylene, and polypropylene.

21. The device of claim 14, further comprising:
third and fourth opposing support members attached to said second end of the vessel connection member.

22. The device of claim 14, wherein said support members are at least one of embedded within, attached directly to, and adhered to said vessel connection member.

23. The device of claim 14, wherein said support members are formed unitary to said vessel connection member.

24. A kit for interconnecting first and second vessels, said kit comprising:
at least one device comprising:
a vessel connection member having a fluid communication lumen extending between first and second openings formed, respectively, at first and second ends of the vessel connection member, wherein said first and second ends are each insertable into said first and second vessels, respectively; and
first and second pairs of support members, each pair of support members consisting of two single loops attached to substantially opposing sides of said first and second openings in said first and second ends of the vessel connection member, respectively, wherein each of the support members are sufficiently flexible so as to angularly adjust with respect to a longitudinal axis of said vessel connection member and to substantially conform to the inner surface of said first and second vessels to exert a force against the vessels to substantially fix the device in an operative position relative to said vessels; and
at least one delivery device for delivering said at least one substance to a target site.

25. The kit of claim 24, further comprising:
a sealing member attached to at least one of an outer perimeter of said vessel connection member adjacent to the first opening so that, when in an operative position, said sealing member forms a substantially fluid-tight seal around said first opening.

26. The kit of claim 24, wherein said sealing member comprises at least one of a flexible flange and an adhesive.

27. The kit of claim 24, wherein said wherein said first and second support members are at least one of embedded within, attached directly to, and adhered to said vessel connection member.

28. The kit of claim 24, further comprising:
instructions for using said at least one device for interconnecting two said first and second vessels.

29. The kit of claim 24, wherein said support members are configured to self-adjust to the inner surface of said first vessel.

30. The kit of claim 24, wherein said support members comprise shape memory material.

31. The kit of claim 30, wherein said shape memory material comprises one of at least shape memory metal and high modulus polymers.

32. The kit of claim 24, wherein said support members are formed unitary to said vessel connection member.

* * * * *